US012156826B2

(12) United States Patent
Ferrigolo et al.

(10) Patent No.: US 12,156,826 B2
(45) Date of Patent: Dec. 3, 2024

(54) FOOTWEAR FOR ORTHOPEDIC OR SPORTS USE

(71) Applicant: F.G.P. S.r.l., Dossobuono (IT)

(72) Inventors: Moreno Ferrigolo, Dossobuono (IT); Alberto Turrini, Dossobuono (IT); Luca Dalla Paola, Faenza (IT)

(73) Assignee: F.G.P. S.r.l., Dossobuono (IT)

( * ) Notice: Subject to any disclaimer, the term of this patent is extended or adjusted under 35 U.S.C. 154(b) by 399 days.

(21) Appl. No.: 17/836,248

(22) Filed: Jun. 9, 2022

(65) Prior Publication Data

US 2022/0401246 A1 Dec. 22, 2022

(30) Foreign Application Priority Data

Jun. 18, 2021 (IT) .................. 102021000015956

(51) Int. Cl.
*A61F 5/01* (2006.01)
*A43B 5/04* (2006.01)

(52) U.S. Cl.
CPC .......... *A61F 5/0195* (2013.01); *A43B 5/0427* (2013.01)

(58) Field of Classification Search
CPC ........ A61F 5/0195; A61F 5/01; A61F 5/0102; A61F 5/0104; A61F 5/0113; A61F 5/0111; A61F 5/0116; A61F 5/0127; A61F 2005/0134; A61F 2005/0137; A61F 2005/0141; A61F 2005/0148; A43B 5/0429; A43B 5/0427; A43B 5/0431; A43B 5/0435; A43B 5/0437; A43B 5/0439; A43B 5/0441; A43B 5/0443; A43B 5/0445

See application file for complete search history.

(56) References Cited

U.S. PATENT DOCUMENTS

2006/0064902 A1* 3/2006 Ashton .................. A43B 23/24
36/94

FOREIGN PATENT DOCUMENTS

| DE | 0824943 A1 * | 8/1997 | |
|----|----|----|----|
| DE | 102013100918 A1 * | 7/2014 | ............ A43B 5/0427 |
| DE | 102016108129 A1 * | 11/2017 | ............ A43B 11/00 |
| DE | 102016108129 B4 * | 5/2018 | ............ A43B 11/00 |
| EP | 0824943 A1 | 2/1998 | |
| EP | 3127446 A1 * | 2/2017 | |
| EP | 3763235 A1 * | 1/2021 | ............ A43B 23/08 |
| WO | WO-2013037924 A1 * | 3/2013 | ............ A43B 13/226 |
| WO | WO-2019169836 A1 * | 9/2019 | ............ A43B 23/08 |

OTHER PUBLICATIONS

Italian Search Report issued for IT Application No. 202100015956 and English translation of Supplemental Report (7 pages).

* cited by examiner

*Primary Examiner* — Tarla R Patel
(74) *Attorney, Agent, or Firm* — ArentFox Schiff LLP

(57) ABSTRACT

A boot-type orthopedic or sports footwear usable for controlled walking with stiffening for the lower extremities of legs, comprises:
a sole provided with a substantially vertical rear positioning element;
a first pair of rear half-hulls, each of which is hinged onto the sole and which cover, when in the closed position, an ankle and part of the lower portion of a leg, i.e. the calcaneal-tibial-tarsal zone, of an individual who is wearing the footwear;
a second pair of front half-hulls, each of which is hinged onto the sole and which cover, when in the closed position, at least an upper part of a foot of the individual who is wearing the footwear.

14 Claims, 7 Drawing Sheets

FOOTWEAR FOR ORTHOPEDIC OR SPORTS USE

TECHNICAL FIELD

The present disclosure relates to boot-type footwear usable for controlled walking with stiffening of the lower extremities of the legs in the case of orthopedic use, or as sports footwear of the mountain boot type, and in particular ski boots, in the case of sports use.

The characteristic shared by the two possible uses of the boot-type footwear according to this disclosure derives from the need to facilitate the operations of putting the footwear on the foot by avoiding having to introduce it with the known systems of opening boots, which are generally very inconvenient and for this reason oblige the user to perform maneuvers that are often rather laborious.

According to the disclosure it is envisaged that the footwear uses a sole, provided with a heel support element, hinged onto the edges of which there are opposite half-parts covering the ankle, the foot and the tibial/peroneal part of the leg, and which are divided along a vertical plane lying on the longitudinal centerline, allowing each of them to go from an open position, with the sole completely free, to a closed one, in a manner substantially like a book.

The footwear according to this disclosure has application in the medical or sports industry, with particular reference to manufacturers of prostheses and braces.

BACKGROUND ART

It is well known that some degenerative diseases such as diabetes cause several complications, among the most frequent of which is a condition known as "diabetic foot"; the latter is the result of complications affecting blood circulation and the peripheral nervous system, whereby the bones and joints of the foot tend to weaken, with the formation of new pressure points in which the skin may become damaged, resulting in wounds.

In the orthopedic industry a need is felt to make things easier for people who suffer from these and other pathologies affecting the lower limbs, and the technology in this sector is increasingly looking for solutions aimed at the production of comfortable footwear which on the one hand allows the feet to be easily introduced and on the other hand assures the necessary support and utmost breathability, in order to enable comfortable walking while avoiding the formation of pressure ulcers, and at the same time assuring a correct orthopedic aid.

The needs in the sports industry are wholly similar, with industry operators seeking to find mountain boot or ski boot solutions that allow the feet to be easily introduced and assure the necessary support and utmost breathability, in order to offer maximum comfort and safety to users.

In this regard, solutions have been devised which envisage the use of boots comprising opening/closing systems that in some cases provide for the division of the footwear in two or more parts which are hinged together and reciprocally couplable and obtained from complete or partial sectioning of the sole along a median longitudinal plane, or a cut made on an oblique plane passing through the malleolar articulation of the ankle with an opening that divides the tibial portion of the leg into two parts.

In general, such solutions suffer from the common drawback of not allowing the foot to be introduced without effort, since there is not provided any possibility of opening the footwear in such a way as to leave the base portion or hull of the sole completely free.

This means that it is necessary for the user to open the upper part of the boot-type footwear as much as possible, in an attempt to recover the largest amount of space possible for introducing his or her foot, and perform several maneuvers, which are in any case always rather laborious, until completely introducing the foot.

Furthermore, in the prior art solutions there is not provided any possibility of dividing the portion of the upper hulls of the footwear into a number of parts, that is, of separating a front portion thereof from a rear portion in the tibial-tarsal zone, to enable the lateral parts of the brace to be closed in an independent front/rear manner. This possibility would be desirable and reveal to be particularly useful in the event that it is necessary to partially or temporarily retain the front part of the foot, or else leave it at least temporarily open, as in the case of diabetic foot.

SUMMARY

The present disclosure aims to provide boot-type footwear usable for orthopedic purposes for controlled walking with stiffening of the lower extremities of the legs, or sports footwear of the mountain boot type, and in particular ski boots, provided with half-hulls that may be opened and spread apart and then closed and joined back together like a book, so as to allow the foot to be easily introduced, thus creating a condition capable of eliminating or at least reducing the drawbacks highlighted above.

In particular, it is aimed to provide a new type of opening for both an orthopedic and a sports boot that enables, in a first step, the positioning of the foot on the sole while the latter remains completely open and free of lateral obstacles, and, in a second step, the rearward movement of the foot until the calcaneal zone is resting against a heel support element.

Furthermore, the footwear according to this disclosure aims to enable closure, following the facilitated positioning of the foot, by joining pairs of lateral half-hulls to the sole, the half-hulls being hinged onto two opposite lateral edges thereof.

Accordingly, it is envisaged that in the open position the same lateral half-hulls enable the introduction of the foot, which goes to rest on the completely open, obstacle-free sole, whereas in the closed position it enables the complete containment of the lower part of the leg, including the tibial-tarsal zone and the foot.

This is obtained by means of boot-type footwear usable for orthopedic purposes for controlled walking with stiffening of the lower extremities of the legs, whose features are described in the main claim.

The dependent claims outline advantageous forms of embodiment.

The main advantages of this solution ultimately regard the fact that the footwear comprises a sole provided with a heel support element, hinged onto whose edges there are half-hulls which are positioned opposite relative to the longitudinal centerline of the sole itself and disposed so as to cover the ankle, the foot and the tibial/peroneal part of the leg, while enabling the boot to be put on with very simple operations that avoid the need to introduce the foot into very limited spaces of the known boots.

Said half-hulls are symmetrically opposite relative to the centerline of the sole and are formed by dividing the upper, that is, the part of the boot above the sole, along a vertical plane lying on the longitudinal centerline of the sole itself, thus enabling each of the half-hulls to go from an open position with the sole completely free to a closed one, by bringing them reciprocally near in a substantially book-like manner.

ILLUSTRATION OF THE DRAWINGS

Other features and advantages will be clear after a reading of the following description of one embodiment, provided by way of non-limiting example with the aid of the figures illustrated in the appended drawings, in which:

FIGS. 4 to 4*d* illustrate schematic views showing an equal number of steps of use of the footwear according to this disclosure in the embodiment as per FIG. 3;

FIGS. 5 to 5*c* and 6 to 6*d* are views of footwear according to this disclosure in a further embodiment thereof wherein the upper comprises front half-hulls with a closed toe made up of two pairs of half-hulls;

DETAILED DESCRIPTION

Figure 1:
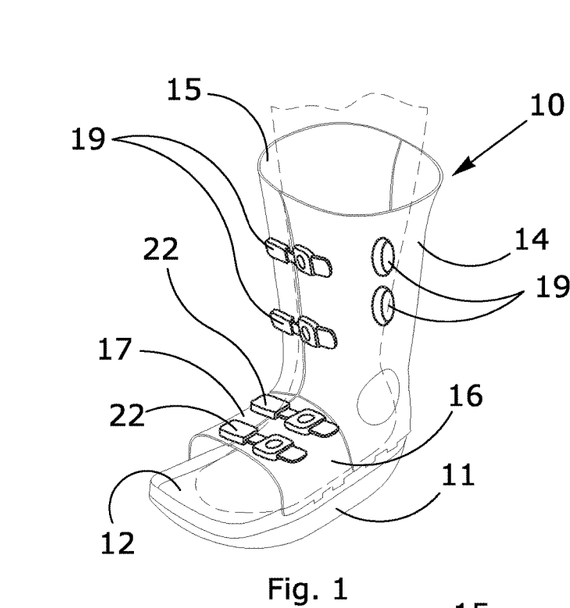
FIGS. 1 to 1*c* represent schematic views of footwear shown from different angles and according to a first embodiment with an open toe and the upper made up of two pairs of half-hulls and an open toe.
Figure 1A:
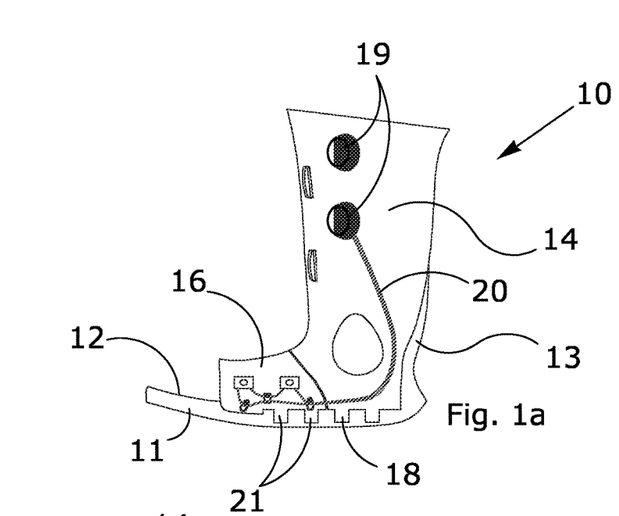
Figure 1B:
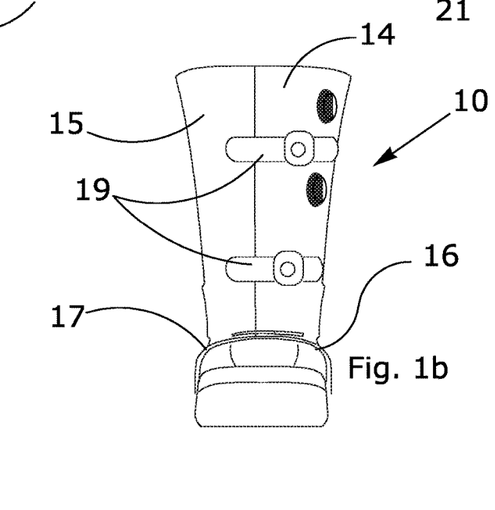
Figure 1C:
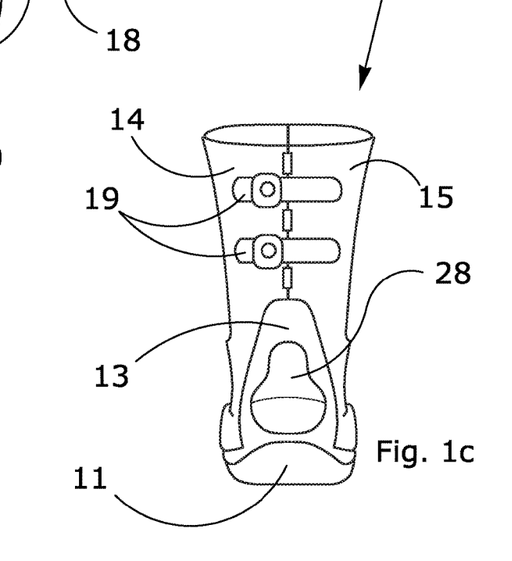

Making reference to the appended figures, and initially in particular to FIGS. 1 to 1*c*, numeral 10 generally indicates a boot designed for orthopedic use or for sports use, according to particular embodiments.

In particular according to the embodiment represented in the aforesaid figures, the boot 10 is made up of a sole 11 comprising on the top thereof a resting base 12 for the foot, provided with a rear positioning element 13 extending substantially vertically and configured as a rear positioning element for the foot, a first pair of rear half-hulls 14 and 15 having a conformation such as to enclose, once joined, the calcaneal-tibial-tarsal portion of the leg and the vertically extending rear positioning element 13, and a second pair of front half-hulls 16 and 17 which cover, once joined, at least an upper part of the foot.

In other words, the two pairs of half-hulls 14 and 15, 16 and 17 are obtained by sectioning the upper on the median vertical plane lying along the longitudinal centerline of the sole.

More precisely, each of the rear half-hulls 14 and 15 comprises a lower edge 18 associated with the rear lateral edge of the base 12 of the sole 11 by means of a hinging configured to allow the respective half-hulls 14 and 15 of to go from an open position, in which they are spread completely apart and nearing the plane in which the sole lies, to a closed position in which the two half-hulls are reciprocally joined with interlocking edges, comprising said rear positioning element 13 of the sole.

The hinging between the two half-hulls and the rear lateral edges of the base 12 is advantageously achieved by means of hinges with pins passing through axes parallel to the edges of the base, or with weakening zones if the boot is made of plastic material in a single mold.

The joining between the two half-hulls 14 and 15 is assured by fixing devices 19 represented by clasp-type elements with adjustment teeth or ratchet-type elements with pull cables 20 connected to pre-established connection points, based on the different needs.

According to a first embodiment represented in FIGS. 1 to 3*d*, each of the front half-hulls 16 and 17, which cover, once joined, at least an upper part of the foot, has a substantially curved shape and comprises a lower edge 21 associated with the front lateral edge of the base 12 of the sole 11 by means of a hinging configured to allow the respective front half-hulls 16 and 17 to go from an open position in which they are spread completely apart and nearing the plane in which the sole lies, to a closed position in which the two half-hulls are reciprocally joined with the interlocking edges thereof.

In this case as well, the joining between the two front half-hulls 16 and 17 is assured by tensioning devices represented by clasp-type elements with adjustment teeth or ratchet-type elements with pull cables connected to pre-established connection points, based on needs.

The hinging between the two front half-hulls 16 and 17 and the rear lateral edges of the base 12 is achieved by means of hinges with pins passing through axes parallel to the edges of the base or with weakening zones if the boot is made of plastic material in a single mold.

Figure 2:
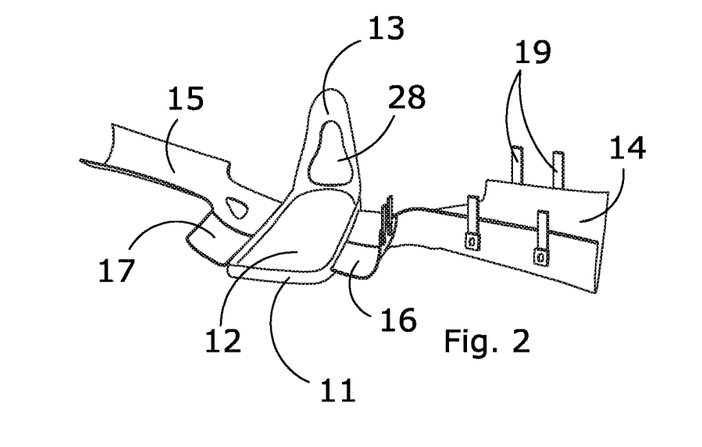
FIGS. 2 to 2*d* illustrate schematic views showing an equal number of steps of use of the footwear according to this disclosure.
Figure 2A:
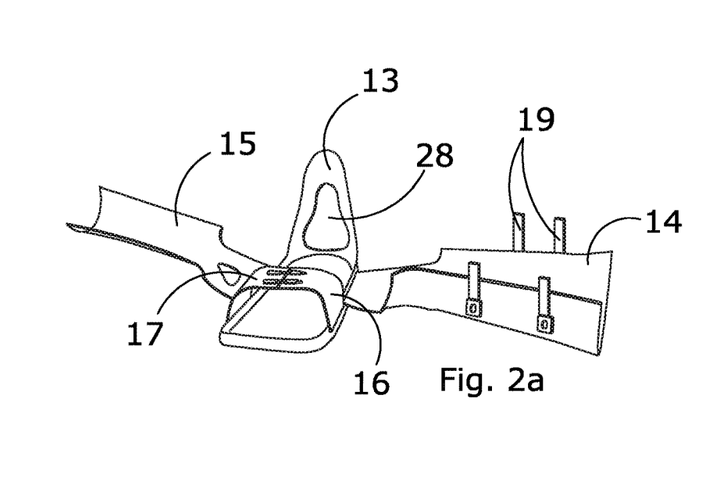
Figure 2B:
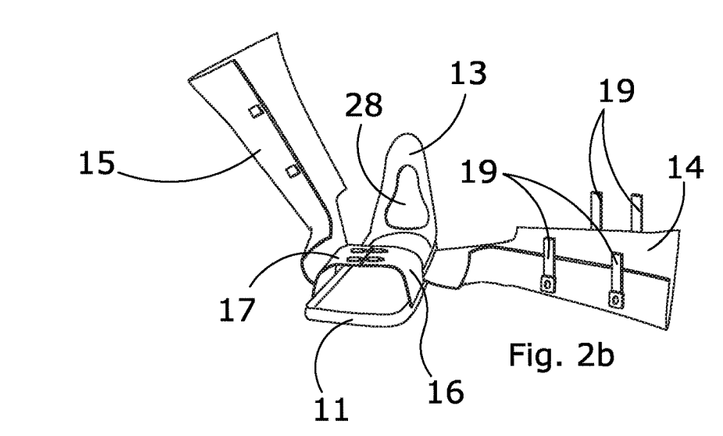
Figure 2C:
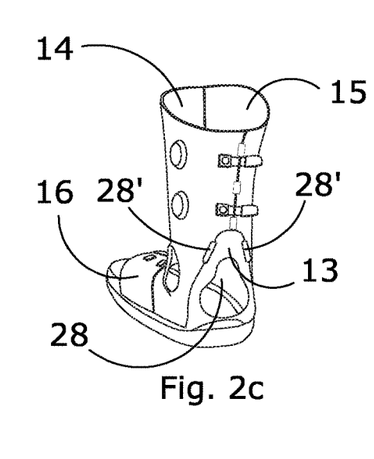
Figure 2D:
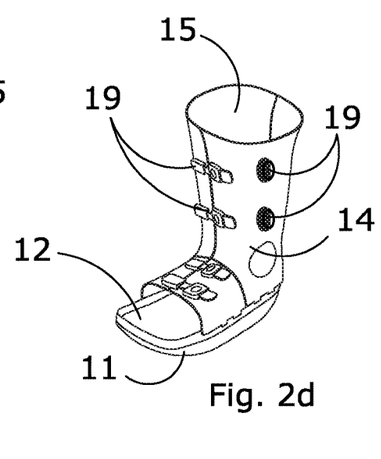
Figure 3:
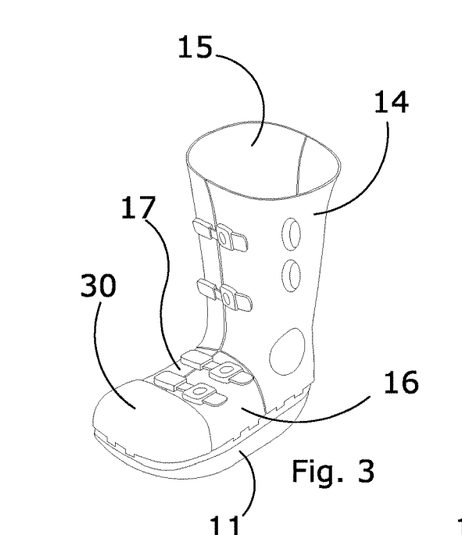
FIGS. 3 to 3*c* are views of footwear according to the invention in an embodiment with a closed toe and upper made up of two pairs of half-hulls and a closed toe.
Figure 3A:
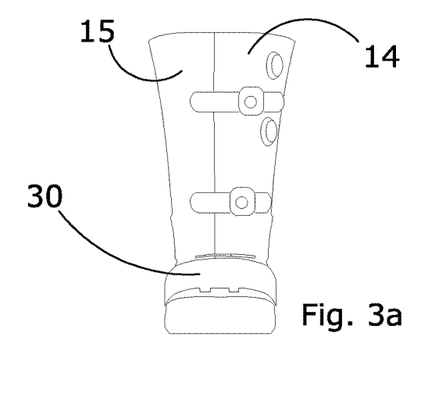
Figure 3B:
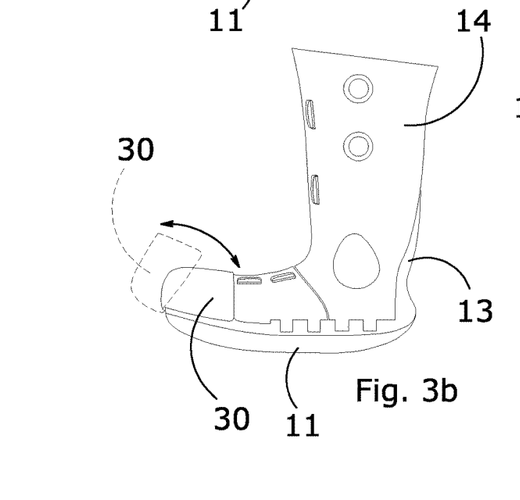
Figure 3C:
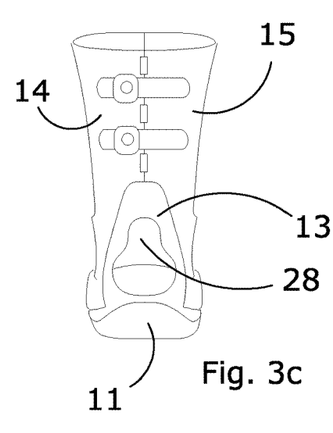

For the use of the boot-type footwear according to said first embodiment, as represented in FIGS. 2 to 2*d*, the first step entails resting the foot on the base 12 of the sole 11 while the half-hulls are disposed in the open position and moving the foot rearward until the heel is resting against the rear positioning element 13. Once the foot is positioned, one proceeds to close the second pair of front half-hulls 16 and 17 (FIG. 2*a*), then to close the pair of rear half-hulls 14 and 15 (FIG. 2*b*), and finally to secure all of the components by means of the fixing devices 19.

According to a second embodiment represented in FIGS. 3 to 3*c* and 4 to 4*d*, the footwear according to the invention—which comprises a sole 11, said two first opposing rear half-hulls 14 and 15 and said two second opposing front half-hulls 16 and 17—also comprises a further front hull 30, hinged onto the front part of the sole and which, in the closed position, covers the front part of the foot and is joined to the second pair of front half-hulls.

In this case the further front hull 30 has a rounded conformation configured to allow the rotation thereof from an open position towards the front part of the sole to an interlocked closed position against the edges of the second front half-hulls 16 and 17.

Figure 4:
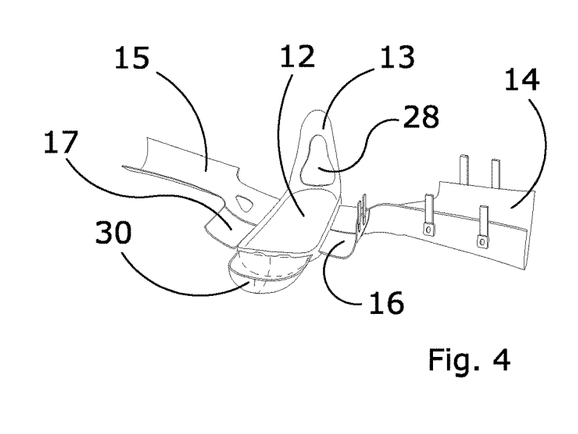
Figure 4A:
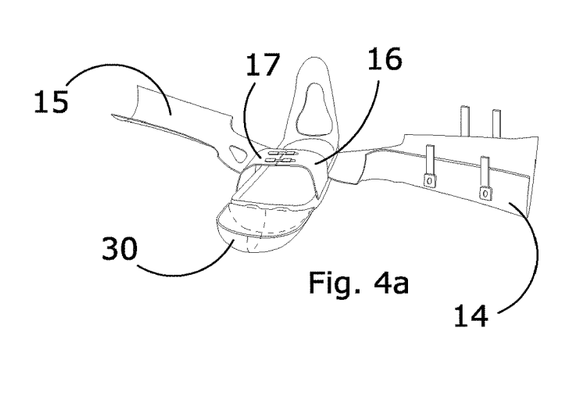
Figures 4B, 4C, 4D:
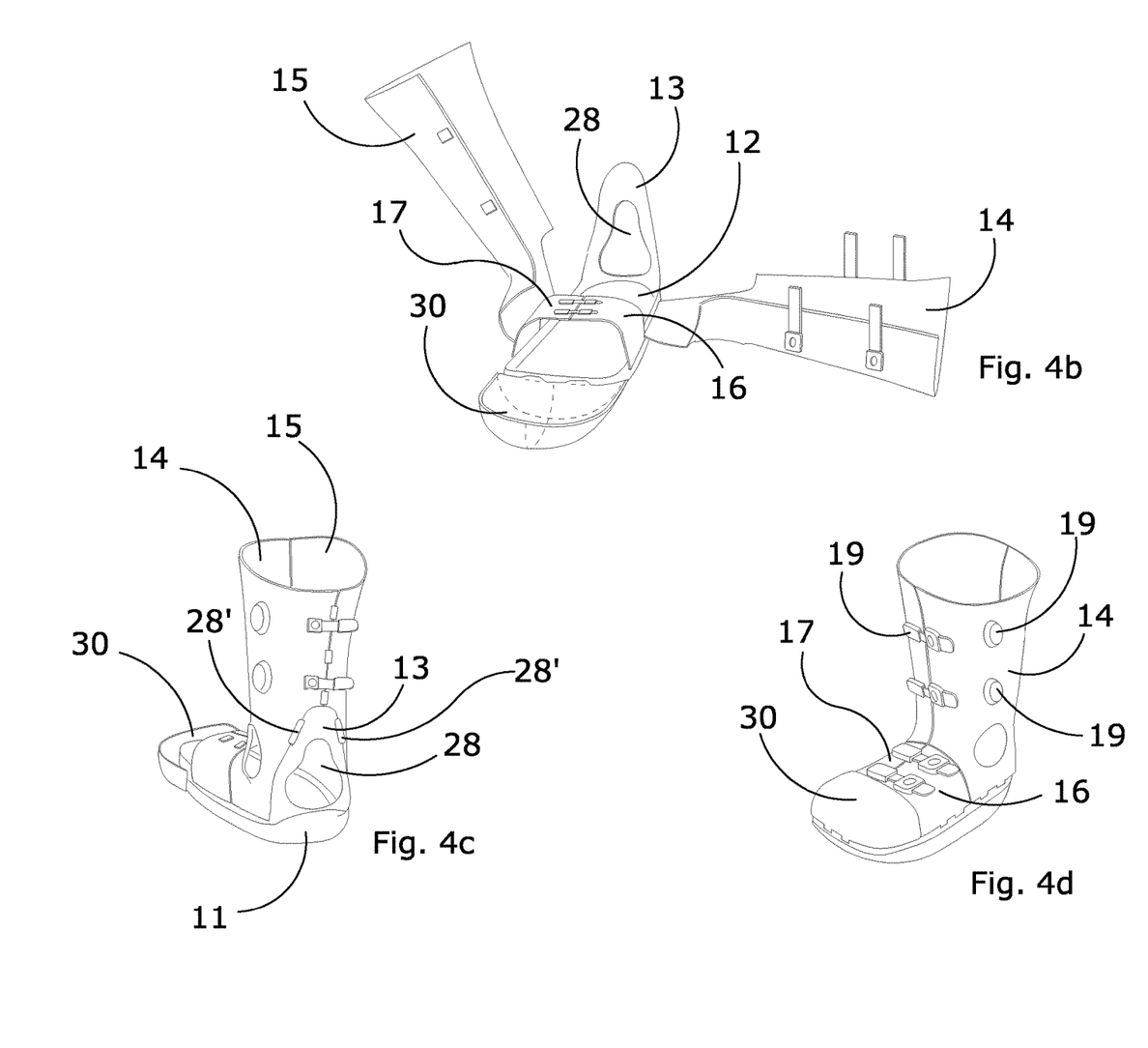
Figures 5, 5B:
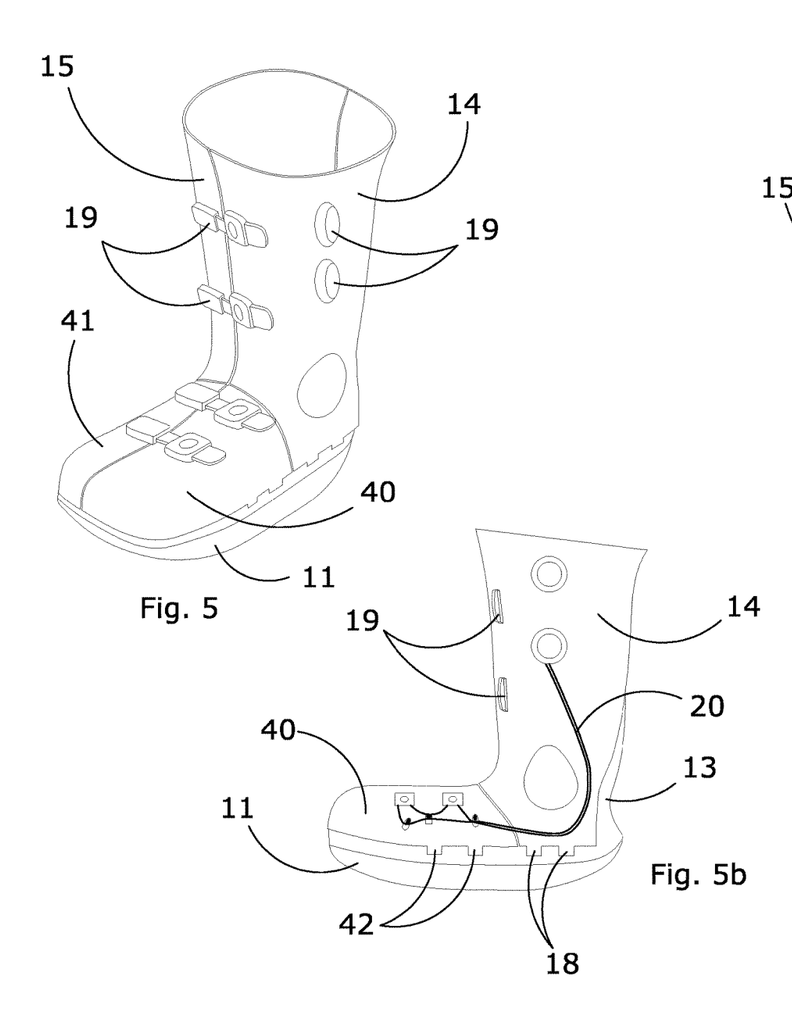
Figure 5A:
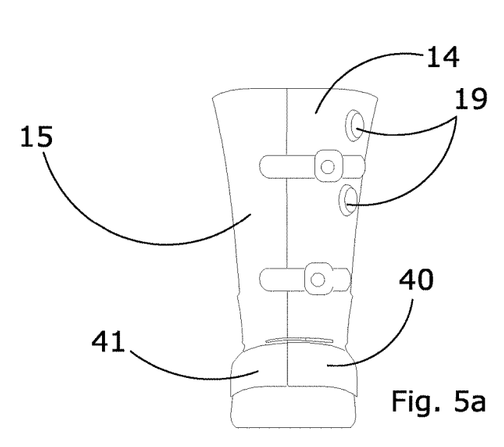
Figure 5C:
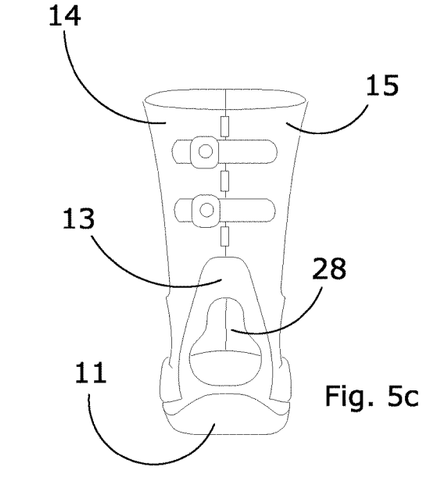

FIGS. 4 to 4*d* illustrate different operating steps of the boot, from a totally open position for the introduction of the foot (FIG. 4), to a first closure of the front half-hulls 16 and 17 (FIG. 4*a*), to a further closure also of the rear half-hulls 14 and 15 (FIG. 4*b*) and the closure of the front hull 30 by interlocking against the edges of the same front half-hulls, followed by fastening by means of the fixing devices 19 (FIG. 4*d*).

According to a third further embodiment that is more suitable as a solution for sports use, for example as a ski boot, represented in FIGS. 5 to 5*c* and 6 to 6*d*, the boot-type footwear comprises a first pair of half-hulls 14 and 15, and a second pair of front half-hulls 40 and 41 which, during use, cover the entire foot, including the area of the tips of the toes.

Figures 6, 6A:
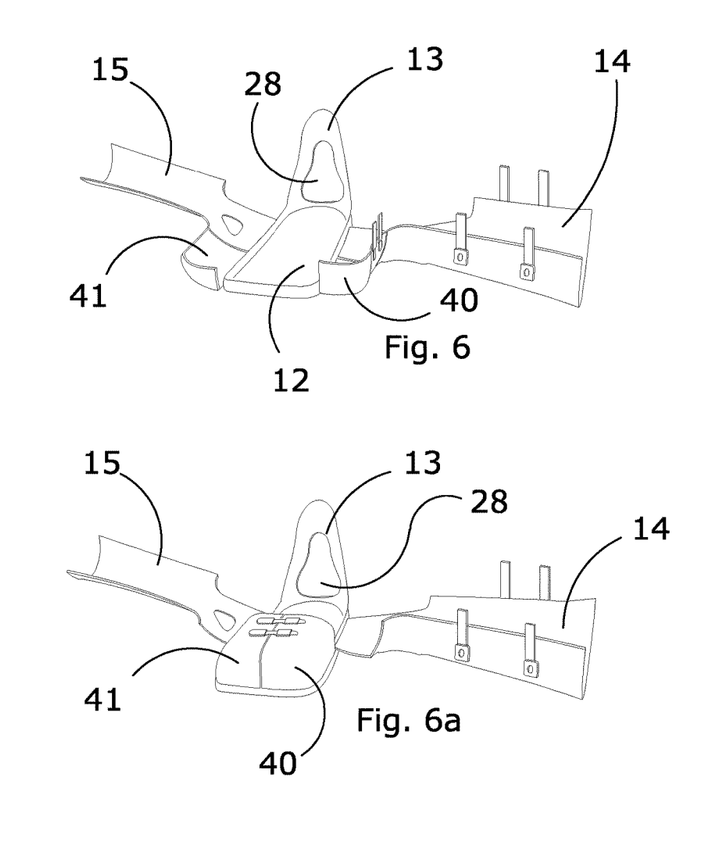
Figure 6B:
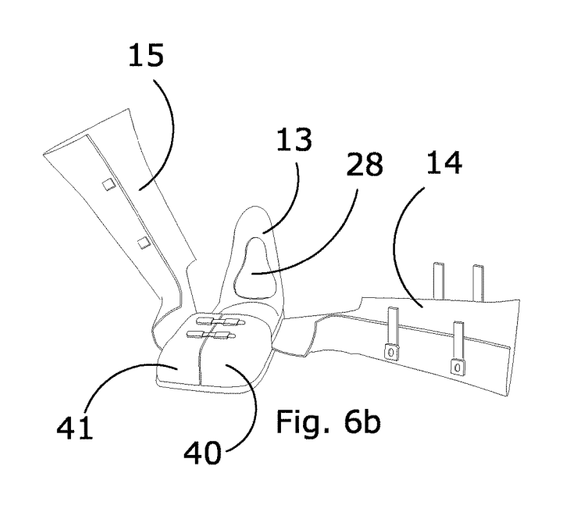
Figure 6C:
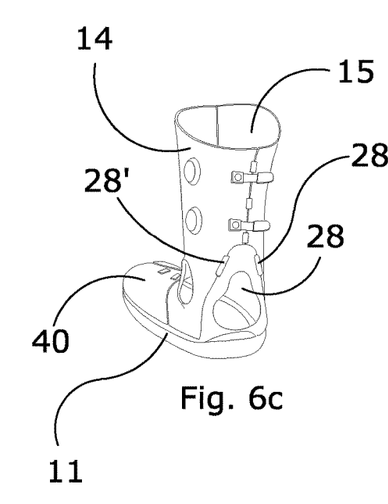
Figure 6D:
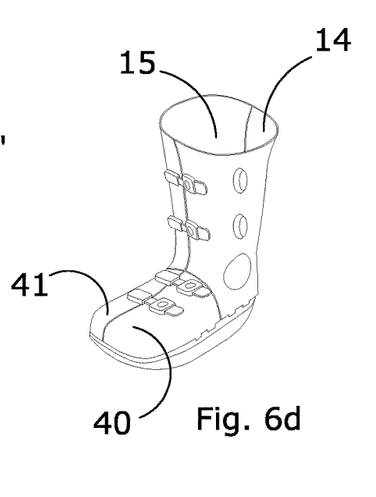

In this case as well, the two pairs of half-hulls 40 and 41 are obtained by sectioning the upper on the median vertical plane lying along the longitudinal centerline of the sole and they are configured so as to comprise respective lower edges 42 associated with the lateral edges of the sole 11 by means of a hinging configured to allow the respective half-hulls 40 and 41 to go from an open position, in which they are spread completely apart and nearing the plane in which the sole lies, to a closed position in which the two half-hulls are reciprocally joined with the interlocking edges thereof, as represented in FIGS. 6 to 6*d*.

As in the preceding cases, the joined parts are maintained in a locked position by means of the fixing devices 19.

Figure 7:
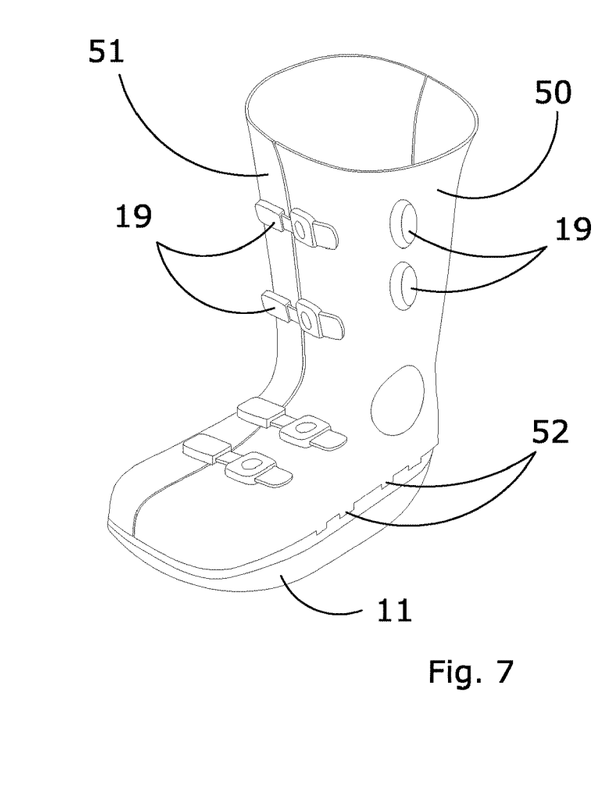
FIGS. 7 and 7*a* regard a solution wherein the upper applied on the sole is divided into two parts consisting of a front half-hull and a rear half-hull which are integral with each other and cover, in the closed position, the entire foot and the lower part of the leg.
Figure 7A:
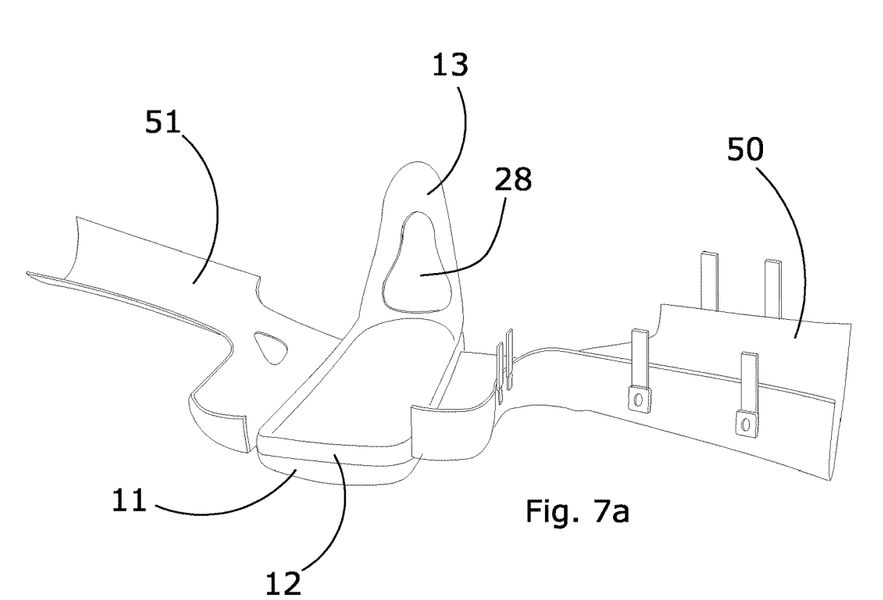

According to the embodiment represented in FIGS. 7 and 7*a*, the upper applied on the sole 11 is divided into two half-parts, and comprises a front half-hull and a rear half-hull, which are integral with each other, thus forming two half-hulls 50 and 51 which cover, in the closed position, the entire foot and all of the calcaneal-tibial-tarsal zone, i.e. the lower part of the leg.

From an operational viewpoint, the two half-hulls 50 and 51 are obtained by sectioning the upper on the median vertical plane lying along the longitudinal centerline of the sole 11 and they are configured so as to comprise respective lower edges 52 associated with the lateral edges of the sole 11 by means of a hinging configured to allow the respective half-hulls 50 and 51 to go from an open position in which they are spread completely apart and nearing the plane in which the sole lies, to a closed position, following the introduction of the foot, in which the two half-hulls are reciprocally joined with the interlocking edges thereof.

According to further embodiments, said rear positioning element 13 extending substantially vertically, configured as a rear positioning element for the foot, is provided with an opening 28 configured as a relief zone for the heel and the tendon associated therewith.

Furthermore, different fixing devices 19 are also provided, in addition to the ones described and illustrated, such as straps, also of the Velere hook and loop fastener type, associated with specific loops, or toothed tabs, wheels and steel cables, or the like.

The hinges connecting the half-hulls to the soles are also made in different ways, in addition to the ones described that use through pins or weakening zones.

The zones in which the half-hulls are joined can also be of various kinds, such as of the interlocking type or another suitable system adapted to join the half-hulls.

According to a possible configuration represented in FIG. 2*c*, the rear edges of the two half-hulls 14 and 15 are provided with lead-in tabs 28' which allow the edges of the rear positioning element 13 of the heel provided with a relief opening 28 to be perfectly contained and retained.

This disclosure has been previously described some preferred forms of embodiment. However, it is clear that there are numerous possible variants falling within the scope of the appended claims.

The invention claimed is:

1. A boot-type orthopedic or sports footwear usable for controlled walking and adapted to stiffen a lower extremity of a leg of an individual, comprising:
   a sole having an upper resting base for a foot;
   a substantially vertical rear element for facilitating positioning of the foot on the upper resting base of the sole;
   a first pair of rear half-hulls, each of which comprises a lower edge hinged to a rear lateral edge of the sole so that each of the rear half-hulls can rotate from an open position in which the first pair of rear half-hulls are spread completely apart relative to the sole, to a closed position in which the first pair of rear half-hulls are reciprocally joined to each other along an edge on a plane passing through a centerline of the sole, and are further connected to an edge of the substantially vertical rear element so as to be able to cover an ankle and a calcaneal-tibial-tarsal zone of a leg of the individual;
   a second pair of front half-hulls, each of which comprises a lower edge hinged to a front lateral edge of the sole so that each of the second pair of front half-hulls can rotate from an open position in which the second pair of front half-hulls are spread completely apart relative to the sole, to a closed position in which the second pair of front half-hulls are reciprocally joined to each other along an edge on a plane passing through the centerline of the sole, and are further connected to the first pair of rear half-hulls so as to be able to cover an upper part of the foot.

2. The footwear of claim 1, comprising a further front hull, hinged onto a front part of the sole and which, in a closed position, covers a front part of the foot and is joined to the second pair of front half-hulls.

3. The footwear of claim 1, wherein the second pair of front half-hulls is adapted to cover the foot, including an area of the tips of the toes of the foot.

4. The footwear of claim 1, wherein each front half-hull and each rear half-hull of each pair are integrated with one another to form two half-hulls which cover, in the closed position, the foot.

5. The footwear of claim 1, wherein each of the first pair of rear half-hulls comprises a hinge associated with the lower edge and the rear lateral edge of the upper resting base of the sole that is configured to allow the respective first pair of half-hulls to go from an open position, in which they are spread completely apart and nearing a plane in which the sole lies, to a closed position in which the first pair of rear half-hulls are reciprocally joined with interlocking edges, comprising the substantially vertical rear element.

6. The footwear of claim 1, wherein each of the second pair of front half-hulls, which cover, once joined, at least an upper part of the foot, has a substantially arched shape and comprises a hinge associated with the lower edge and the front lateral edge of the upper resting base of the sole that is configured to allow the respective second pair of front half-hulls to go from an open position, in which they are spread completely apart and nearing a plane in which the sole lies, to a closed position in which the second pair of half-hulls are reciprocally joined with their interlocking edges.

7. The footwear of claim 1, comprising a further front hull, hinged onto the front part of the sole and which, in the closed position, covers a front part of the foot and is joined to said second pair of front half-hulls.

8. The footwear of claim 1, wherein the substantially vertical rear element is provided with an opening configured as a relief zone for a heel and a tendon associated therewith of the individual wearing the footwear.

9. The footwear of claim 1, comprising a padding system to cushion the foot and an ankle of the individual wearing the footwear, positionable inside the first and second pairs of half-hulls and the sole.

10. The footwear of claim 1, wherein the first and second pairs of half-hulls are joined together and fixed by one or more fixing devices with adjustment teeth or ratchet-type elements with pull cables connected to pre-established connection points, straps, also of a hook and loop fastener type, associated with specific loops, or with toothed tabs, wheels and steel cables.

11. The footwear of claim 1, wherein the first and second pairs of half-hulls are connected to the soles by one or more hinges with pins passing through axes parallel to the edges of the upper resting base.

12. The footwear of claim 1, wherein one or more zones joining the first and second pairs of half-hulls are an interlocking or overlapping type.

13. The footwear of claim 1, wherein the rear edges of the first and second pairs of half-hulls are provided with one or more lead-in tabs configured to contain and retain the edges of the substantially vertical element.

14. A boot-type orthopedic or sports footwear usable for controlled walking and adapted to stiffen a lower extremity of a leg of an individual, comprising:
  a sole having an upper resting base for a foot;
  a substantially vertical rear element for facilitating positioning of the foot on the upper resting base of the sole;
  a first pair of rear half-hulls, each of which comprises a lower edge hinged to a rear lateral edge of the sole so that each of the rear half-hulls can rotate from an open position in which the first pair of rear half-hulls are spread completely apart relative to the sole, to a closed position in which the first pair of rear half-hulls are reciprocally joined to each other along an edge on a plane passing through a centerline of the sole, and are further connected to an edge of the substantially vertical rear element so as to be able to cover an ankle and a calcaneal-tibial-tarsal zone of a leg of the individual;
  a second pair of front half-hulls, each of which comprises a lower edge hinged to a front lateral edge of the sole so that each of the second pair of front half-hulls can rotate from an open position in which the second pair of front half-hulls are spread completely apart relative to the sole, to a closed position in which the second pair of front half-hulls are reciprocally joined to each other along an edge on a plane passing through the centerline of the sole, and are further connected to the first pair of rear half-hulls so as to be able to cover an upper part of the foot,
wherein each of the second pair of front half-hulls, which cover, once joined, at least an upper part of the foot, has a substantially arched shape and comprises a hinge associated with the lower edge and the front lateral edge of the upper resting base of the sole that is configured to allow the respective second pair of front half-hulls to go from an open position, in which they are spread completely apart and nearing a plane in which the sole lies, to a closed position in which the second pair of half-hulls are reciprocally joined with their interlocking edges.

* * * * *